United States Patent
Bach et al.

(10) Patent No.: US 6,194,402 B1
(45) Date of Patent: Feb. 27, 2001

(54) ENHANCEMENT OF RETURN TO INDEPENDENT LIVING STATUS WITH A GROWTH HORMONE SECRETAGOGUE

(75) Inventors: Mark Bach, Scotch Plains, NJ (US); Vivian Fuh, New York, NY (US); Jennifer Ng, Short Hills; Alice Taylor, Edison, both of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/386,177

(22) Filed: Aug. 31, 1999

Related U.S. Application Data

(60) Provisional application No. 60/098,869, filed on Sep. 2, 1998.

(51) Int. Cl.[7] ............... A61K 31/55; A61K 31/54; A61K 31/535; A61K 31/50; A61K 31/44
(52) U.S. Cl. ............... 514/212.05; 514/224.2; 514/230.5; 514/248; 514/278
(58) Field of Search ............... 514/224.2, 230.5, 514/248, 278, 212.05

(56) References Cited

U.S. PATENT DOCUMENTS

| 5,206,235 | * | 4/1993 | Fisher et al. | 514/213 |
|---|---|---|---|---|
| 5,283,241 | * | 2/1994 | Bochis et al. | 514/183 |
| 5,536,716 | | 7/1996 | Chen et al. | |
| 5,723,616 | | 3/1998 | Houghton et al. | |
| 5,767,124 | | 6/1998 | Draper et al. | |
| 5,773,441 | | 6/1998 | Hipskind et al. | |

OTHER PUBLICATIONS

Arena, J.P., et al., *Chem. Abstr.*, vol. 127, Abs. No. 117853 (1997).

Carpino, P.A., et al., *Chem. Abstr.*, vol. 127, Abs. No. 14941 (1997).

Lieber, R.L., et al., *Chem. Abstr.*, vol. 127, Abs. No. 342048 (1997).

Murphy, M.G., et al., *Chem. Abstr.*, vol. 128, Abs. No. 226045 (1998).

* cited by examiner

*Primary Examiner*—Kevin E. Weddington
(74) *Attorney, Agent, or Firm*—J. Eric Theis; David L. Rose

(57) ABSTRACT

A growth hormone secretagogue is useful for enhancing the return of patients to independent living status following acute deconditioning such as that which may result from immobilization, surgery, or major injury such as hip fracture.

15 Claims, 2 Drawing Sheets

Figure 1:
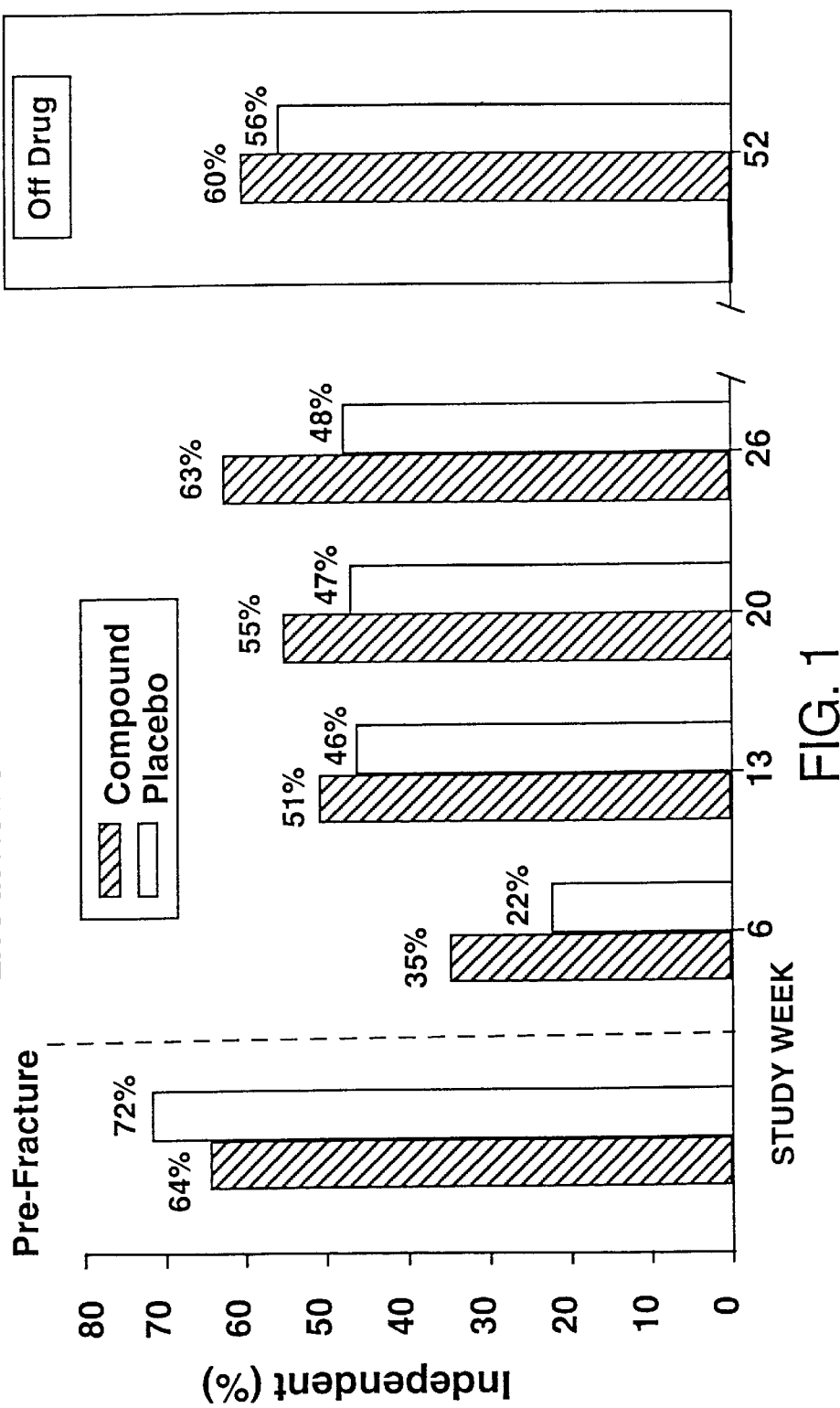

ENHANCEMENT OF RETURN TO INDEPENDENT LIVING STATUS WITH A GROWTH HORMONE SECRETAGOGUE

This application claims the benefit of U.S. Provisional Application No. 06/098,869, filed Sep. 2. 1998.

BACKGROUND OF THE INVENTION

Many patients who receive surgery or experience a major illness or injury require additional care and supervision following such surgery or illness. Patients who receive surgery or experience a major illness or injury such as hip fracture may have prolonged recovery times due to deconditioning, a bed-rest associated syndrome comprising, e.g.: decreased cardiac output, hypotension, muscular atrophy and acute muscle loss, and joint contractures (Hoenig and Rubenstein, *Journal of the American Geriatrics Society*, 39, 220–221. (1991)). In the elderly the loss of muscle mass and function as a result of illness or immobilization may be up to 5% per day at bedrest. Among the elderly in particular, deconditioning associated with acute illness is believed to lead to recovery times far in excess of that expected for the acute illness itself. In addition to prolonged recovery times, functional losses may result from deconditioning, the acute illness itself, and untoward effects of treatment. Although many functional losses are often reversible with activity and exercise interventions, recovery times may vary widely (Vorhies and Riley, *Clinical Geriatric Medicine*, 9, 745–763 (1993)). There are direct and indirect costs associated with both the acute illness and recovery periods. These costs may be considerable.

As a result of their deconditioned physical state, patients who had once been able to live independently may require additional assistance and care. In particular, patients who had previously lived independently in a private home or apartment may find that following surgery or a major illness or injury they require the formal care provided by an assisted living center, a nursing home, a rehabilitation hospital/center, an acute care hospital or a chronic medical care center.

This increase in the degree of care which is required by an individual following such deconditioning imposes increased financial costs. Moreover, such restrictions in their lifestyle may impose detrimental psychological impact with respect to the patient's self esteem and independence.

Many patients suffering from acute deconditioning, such as following a hip fracture, never regain their premorbid level of function. The recovery of a patient following a hip fracture as represented by their independent living status is generally a very difficult process. Data on the percentage of patients living independently following a hip fracture has been presented (Jette, et al., *Arch. Phys. Med. Rehab.*, 68:735 (1987)). Approximately 48% of the patients studied were living independently prior to their hip fracture. Immediately following reconstructive hip surgery only about 5% were living independently; at 3 months and at 6 months after their hip fracture only about 25% were living independently; and at 12 months after their hip fracture only about 22% were living independently.

Very few compounds are known in the art to be useful for the enhancing the return of patients to independent living status following deconditioning. Moreover, these therapeutic regimens suffer from numerous problems and a more effective, physiological way to enhance the return of patients to independent living status following deconditioning would be highly desirable.

Growth hormone, which is secreted from the pituitary, stimulates growth of all tissues of the body that are capable of growing. In addition, growth hormone is known to have the following basic effects on the metabolic processes of the body: (1) Increased rate of protein synthesis in all cells of the body; (2) Decreased rate of carbohydrate utilization in cells of the body; (3) Increased mobilization of free fatty acids and use of fatty acids for energy.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known growth hormone secretagogue growth hormone releasing factor (GRF) or an unknown endogenous growth hormone-releasing hormone or all of these.

In cases where increased levels of growth hormone were desired, the problem was generally solved by providing exogenous growth hormone or by administering GRF, IGF-I or a peptidal compound which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recombinant growth hormone has become available which, while no longer carrying any risk of disease transmission, is still a very expensive product which must be given by injection or by a nasal spray. In addition, administration of exogenous growth hormone may result in side-effects, including edema, and does not correlate with the pulsitile release seen in the endogenous release of growth hormone.

Certain compounds have been developed which stimulate the release of endogenous growth hormone. Peptides which are known to stimulate the release of endogenous growth hormone include growth hormone releasing hormone, the growth hormone releasing peptides GHRP-6 and GHRP-1 (described in U.S. Pat. No. 4,411,890, PCT Patent Pub. No. WO 89/07110, and PCT Patent Pub. No. WO 89/07111) and GHRP-2 (described in PCT Patent Pub. No. WO 93/04081), as well as hexarelin (*J. Endocrinol Invest.*, 15(Suppl 4), 45 (1992)). Other compounds possessing growth hormone secretagogue activity are disclosed in the following: U.S. Pat. No. 3,239,345; U.S. Pat. No. 4,036,979; U.S. Pat. No. 4,411,890; U.S. Pat. No. 5,206,235; U.S. Pat. No. 5,283,241; U.S. Pat. No. 5,284,841; U.S. Pat. No. 5,310,737; U.S. Pat. No. 5,317,017; U.S. Pat. No. 5,374,721; U.S. Pat. No. 5,430,144; U.S. Pat. No. 5,434,261; U.S. Pat. No. 5,438,136; U.S. Pat. No. 5,494,919; U.S. Pat. No. 5,494,920; U.S. Pat. No. 5,492,916; U.S. Pat. No. 5,536,716; EPO Patent Pub. No. 0,144,230; EPO Patent Pub. No. 0,513,974; PCT Patent Pub. No. WO 94/07486; PCT Patent Pub. No. WO 94/08583; PCT Patent Pub. No. WO 94/11012; PCT Patent Pub. No. WO 94/13696; PCT Patent Pub. No. WO 94/19367; PCT Patent Pub. No. WO 95/03289; PCT Patent Pub. No. WO 95/03290; PCT Patent Pub. No. WO 95/09633; PCT Patent Pub. No. WO 95/11029; PCT Patent Pub. No. WO 95/12598; PCT Patent Pub. No. WO 95/13069; PCT Patent Pub. No. WO 95/14666; PCT Patent Pub. No. WO 95/16675; PCT Patent Pub. No. WO 95/16692; PCT Patent Pub. No. WO 95/17422; PCT Patent Pub. No. WO 95/17423; PCT Patent Pub. No. WO 95/34311; PCT Patent Pub. No. WO 96/02530; PCT Patent Pub. No. WO 96/05195; PCT Patent Pub. No. WO 96/15148; PCT Patent Pub. No. WO 96/22782; PCT Patent Pub. No. WO 96/22997; PCT Patent Pub. No. WO 96/24580; PCT Patent Pub. No. WO 96/24587; PCT Patent Pub. No. WO 96/35713; PCT Patent Pub. No. WO 96/38471; PCT Patent Pub. No. WO 97/00894; PCT Patent Pub. No. WO 97/06803; PCT Patent Pub. No. WO 97/07117; *Science* 260, 1640–1643 (Jun. 11, 1993); *Ann. Rep. Med. Chem.*, 28,177–186 (1993); *Bioorg. Med. Chem. Ltrs.*, 4(22), 2709–2714 (1994); and *Proc. Natl. Acad. Sci. USA* 92, 7001–7005 (July 1995). Additional compounds with growth hormone secretagogue activity are described herein.

SUMMARY OF THE INVENTION

The present invention is directed to the use of a compound which has the ability to stimulate or amplify the release of natural or endogenous growth hormone for enhancing the return of patients to independent living status following deconditioning, in a warm-blooded animal. The advantage of this method is that in contrast to injections of growth hormone it provides a physiological-like pulsatile profile of growth hormone release from the pituitary gland. Accordingly, the present invention provides a method for enhancing the return of patients to independent living status following deconditioning in a warm-blooded animal comprising the administration of a growth hormone secretagogue. The present invention further provides a pharmaceutical composition for enhancing the return of patients to independent living status following deconditioning.

DETAILED DESCRIPTION OF THE DRAWING

A more complete understanding of the present invention may be obtained by reading the following description in conjunction with the appended figures which like elements are labeled similarly.

FIG. 1 depicts a summary of the data from a double-blind, placebo-controlled, parallel-group study to determine the effect of a growth hormone secretagogue on the return to independent living status in patients suffering a hip fracture. Following their hip fracture, a greater percentage of the patients receiving growth hormone secretagogue were living independently.

Figure 2:
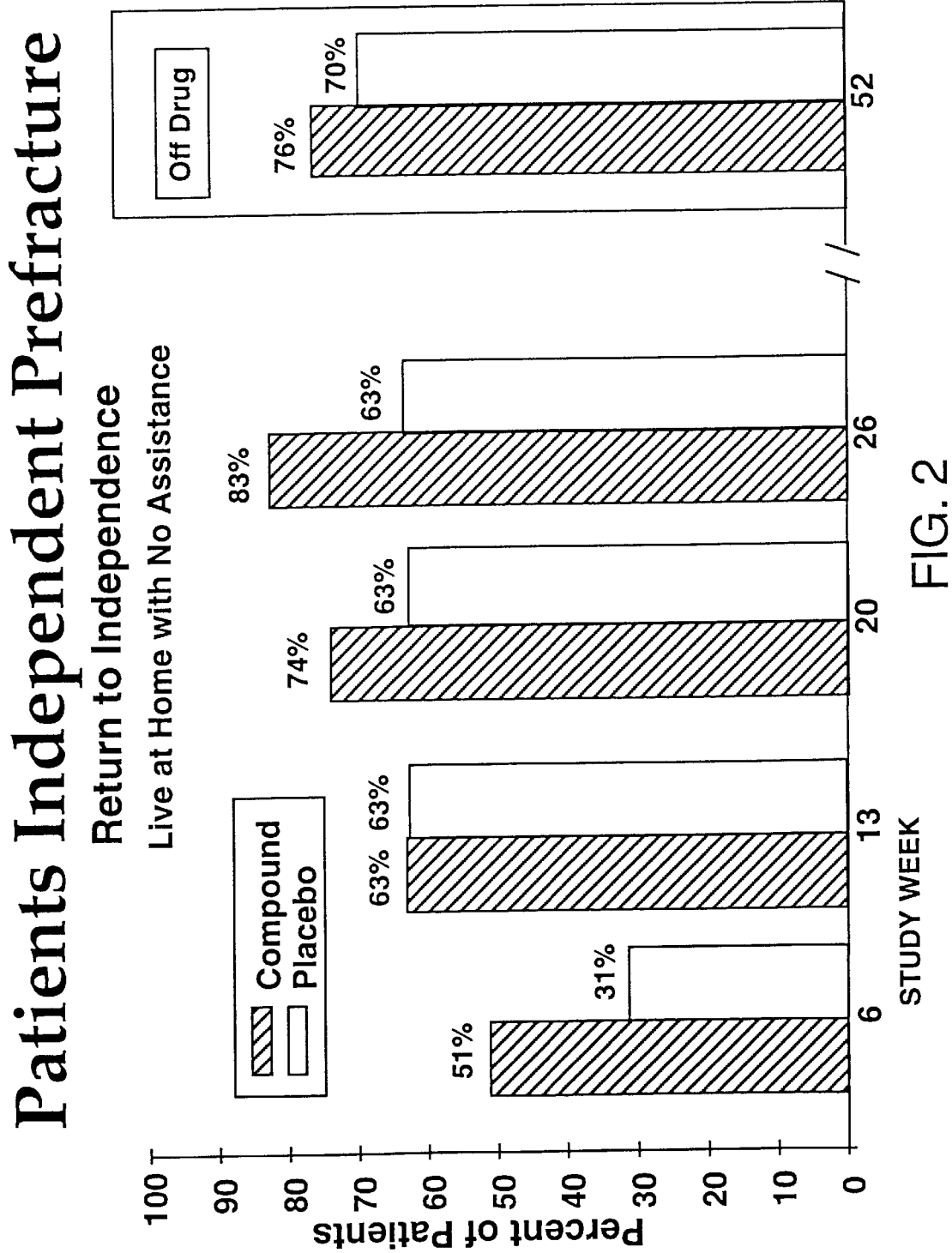

FIG. 2 depicts a summary of the data from a double-blind, placebo-controlled, parallel-group study to determine the effect of a growth hormone secretagogue on the return to independent living status in patients suffering a hip fracture. Of the patients who were living independently prior to their hip fracture, a greater percentage of the patients receiving growth hormone secretagogue returned to independence following their hip fracture.

DETAILED DESCRIPTION OF THE INVENTION

The present invention is directed to the use of a compound which has the ability to stimulate or amplify the release of natural or endogenous growth hormone for enhancing the return of patients to independent living status following deconditioning. In particular, the present invention provides a method for enhancing the return of a patient to independent living status following deconditioning of the patient comprising the administration of a growth hormone secretagogue. In a preferred aspect, the present invention provides a method for enhancing the return of a patient to independent living status following acute deconditioning of the patient comprising the administration of a growth hormone secretagogue.

The present invention is further directed to a method for ameliorating an acute deconditioned physiological state of in a mammal which comprises administering an effective amount of a growth hormone secretagogue. The acute deconditioned physical state in the mammal may result from immobilization, surgery, major injury such as hip fracture or other bone fracture, gunshot wound or automobile accident, and the like. The present invention currently has found greatest application in enhancing the return of patients to independent living status following hip fracture.

In the present invention, it is preferred that the subject mammal is a human. Although the present invention is applicable both old and young people, it may find greater application in elderly people especially people aged 70 years and older.

In a preferred embodiment of the present invention to enhance the return of patients to independent living status following acute deconditioning, therapy with the growth hormone secretagogue is supplemented or employed in conjunction with physical rehabilitation.

In the present invention, it is preferred that the patient be living independently prior to their acute deconditioning. Nevertheless, the present invention may also be applicable in helping patients who were not living independently prior to their acute deconditioning to achieve independent living status.

By the term "growth hormone secretagogue" is meant any exogenously administered compound or agent that directly or indirectly stimulates or increases the endogenous release of growth hormone, growth hormone-releasing hormone or somatostatin in an animal, in particular, a human.

The growth hormone secretagogue may be peptidal or non-peptidal in nature, however, the use of a orally active growth hormone secretagogue is preferred. In addition, it is preferred that the growth hormone secretagogue induce or amplify a pulsatile release of endogenous growth hormone.

The growth hormone secretagogue may be used alone or in combination with other growth hormone secretagogues or with other agents which are known to be beneficial for enhancing the return of patients to independent living status following deconditioning. The growth hormone secretagogue and the other agent may be coadministered, either in concomitant therapy or in a fixed combination. For example, the growth hormone secretagogue may be administered in combination with other compounds which are known in the art to be useful for enhancing the return of patients to independent living status following deconditioning.

Representative growth hormone secretagogues are disclosed in: U.S. Pat. No. 3,239,345; U.S. Pat. No. 4,036,979; U.S. Pat. No. 4,411,890; U.S. Pat. No. 5,206,235; U.S. Pat. No. 5,283,241; U.S. Pat. No. 5,284,841; U.S. Pat. No. 5,310,737; U.S. Pat. No. 5,317,017; U.S. Pat. No. 5,374,721; U.S. Pat. No. 5,430,144; U.S. Pat. No. 5,434,261; U.S. Pat. No. 5,438,136; U.S. Pat. No. 5,494,919; U.S. Pat. No. 5,494,920; U.S. Pat. No. 5,492,916; U.S. Pat. No. 5,536,716; EPO Patent Pub. No. 0,144,230; EPO Patent Pub. No. 0,513,974; PCT Patent Pub. No. WO 89/07110; PCT Patent Pub. No. WO 89/07111; PCT Patent Pub. No. WO 93/04081; PCT Patent Pub. No. WO 94/07486; PCT Patent Pub. No. WO 94/08583; PCT Patent Pub. No. WO 94/11012; PCT Patent Pub. No. WO 94/13696; PCT Patent Pub. No. WO 94/19367; PCT Patent Pub. No. WO 95/03289; PCT Patent Pub. No. WO 95/03290; PCT Patent Pub. No. WO 95/09633; PCT Patent Pub. No. WO 95/11029; PCT Patent Pub. No. WO 95/12598; PCT Patent Pub. No. WO 95/13069; PCT Patent Pub. No. WO 95/14666; PCT Patent Pub. No. WO 95/16675; PCT Patent Pub. No. WO 95/16692; PCT Patent Pub. No. WO 95/17422; PCT Patent Pub. No. WO 95/17423; PCT Patent Pub. No. WO 95/34311; PCT Patent Pub. No. WO 96/02530; PCT Patent Pub. No. WO 96/05195; PCT Patent Pub. No. WO 96/15148; PCT Patent Pub. No. WO 96/22782; PCT Patent Pub. No. WO 96/22997; PCT Patent Pub. No. WO 96/24580; PCT Patent Pub. No. WO 96/24587; PCT Patent Pub. No. WO 96/35713; PCT Patent Pub. No. WO 96/38471; PCT Patent Pub. No. WO 97/00894; PCT Patent Pub. No. WO 97/06803; PCT Patent Pub. No. WO 97/07117; J. Endocrinol Invest., 15(Suppl 4), 45 (1992)); Science 260, 1640–1643 (Jun. 11, 1993); Ann. Rep. Med. Chem., 28, 177–186 (1993); Bioorg. Med. Chem. Ltrs., 4(22), 2709–2714 (1994); and Proc. Natl. Acad. Sci. USA 92, 7001–7005 (July 1995).

A representative first class of growth hormone secretagogues is set forth in U.S. Pat. No. 5,206,235 as follows:

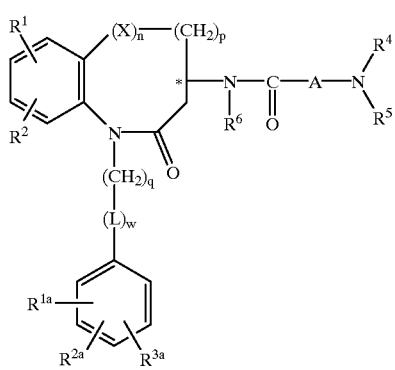

wherein the various substituents are as defined in U.S. Pat. No. 5,206,235.

The most preferred compounds within this first class are identified as having the following structures:

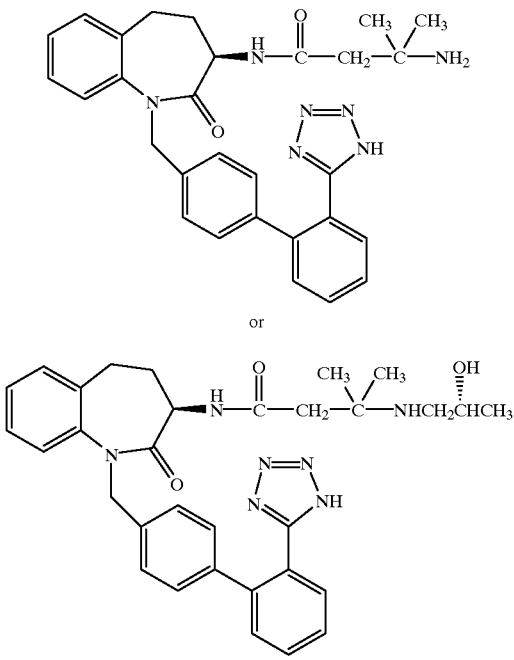

A representative second class of growth hormone secretagogues is set forth in U.S. Pat. No. 5,283,241 and PCT Patent Publication No. 94/05634 as having the following structural formula:

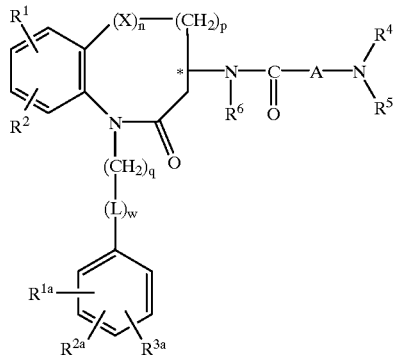

wherein the various substituents are as defined in U.S. Pat. No. 5,283,241 and PCT Patent Publication No. 94/05634.

A representative third class of growth hormone secretagogues is disclosed in U.S. Pat. No. 5,536,716 and PCT Patent Pub. No. WO 94/13696 as compounds of the following structural Formulas I and II:

Formula I

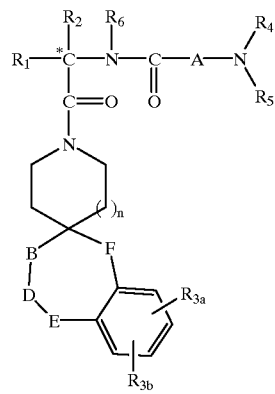

Formula II

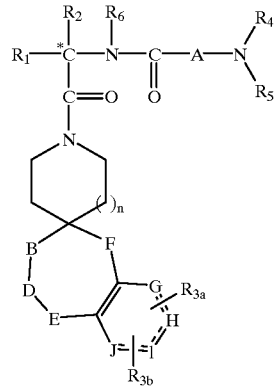

wherein:
$R_1$ is selected from the group consisting of:
—$C_1$–$C_{10}$ alkyl, -aryl, -aryl-($C_1$–$C_6$ alkyl),
—$C_3$–$C_7$ cycloalkyl-($C_1$–$C_6$alkyl), —$C_1$–$C_5$alkyl-K—$C_1$–$C_5$ alkyl,
-aryl($C_0$–$C_5$alkyl)—K—($C_1$–$C_5$ alkyl),
—$C_3$–$C_7$ cycloalkyl($C_0$–$C_5$ alkyl)—K—($C_1$–$C_5$ alkyl), wherein K is O, S(O)$_m$, N(R$_2$)C(O), C(O)N(R$_2$), OC(O), C(O)O, or —CR$_2$=CR$_2$—, or —C≡C—, and wherein the aryl groups are as defined below and the R$_2$ and alkyl groups may be further substituted by 1 to 9 halogen, S(O)mR$_{2a}$, 1 to 3 OR$_{2a}$, or C(O)OR$_{2a}$, and the aryl groups may be further substituted by phenyl, phenoxy, halophenyl, 1–3 C$_1$–C$_6$ alkyl, 1 to 3 halogen, 1 to 2 —OR$_2$, methylenedioxy, —S(O)$_m$R$_2$, 1 to 2 —CF$_3$, —OCF$_3$, nitro, —N(R$_2$)(R$_2$), —N(R$_2$)C(O)R$_2$, —C(O)OR$_2$, —C(O)N(R$_2$)(R$_2$), —SO$_2$N(R$_2$)(R$_2$), —N(R$_2$)S(O)$_2$ aryl, and —N(R$_2$)SO$_2$R$_2$;

R$_2$ is selected from the group consisting of:

hydrogen, C$_1$–C$_6$ alkyl, C$_3$–C$_7$ cycloalkyl, and where two C$_1$–C$_6$ alkyl groups are present on one atom, they may be optionally joined to form a C$_3$–C$_8$ cyclic ring optionally including oxygen, sulfur or NR$_{2a}$;

R$_{2a}$ is hydrogen, or C$_1$–C$_6$ alkyl;

R$_{3a}$ and R$_{3b}$ are independently selected from the group consisting of:

hydrogen, halogen, —C$_1$–C$_6$ alkyl, —OR$_2$, cyano, —OCF$_3$, methylenedioxy, nitro, —S(O)$_m$R, —CF$_3$ or —C(O)OR$_2$ and when R$_{3a}$ and R$_{3b}$ are in an ortho arrangement, they may be joined to form a C$_5$ to C$_8$ aliphatic or aromatic ring optionally including 1 or 2 heteroatoms selected from oxygen, sulfur or nitrogen;

R$_4$ and R$_5$ are independently selected from the group consisting of:

hydrogen, —C$_1$–C$_6$ alkyl, substituted C$_1$–C$_6$ alkyl wherein the substituents are selected from 1 to 5 halo, 1 to 3 hydroxy, 1 to 3 C$_1$–C$_{10}$ alkanoyloxy, 1 to 3 C$_1$–C$_6$ alkoxy, phenyl, phenoxy, 2-furyl, C$_1$–C$_6$ alkoxycarbonyl, —S(O)m(C$_1$–C$_6$ alkyl); or R$_4$ and R$_5$ can be taken together to form —(CH$_2$)$_r$L$_a$ (CH$_2$)$_s$— where L$_a$ is —C(R$_2$)$_2$—, —O—, —S(O)$_m$—, or —N(R$_2$)—, where r and s are independently 1 to 3 and R$_2$ is as defined above;

R$_6$ is hydrogen or C$_1$–C$_6$ alkyl;

A is:

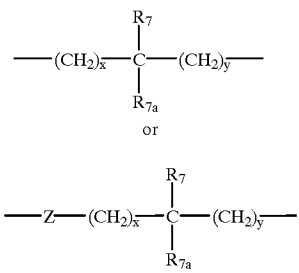

wherein x and y are independently 0–3;

Z is N—R$_2$ or O;

R$_7$ and R$_{7a}$ are independently selected from the group consisting of:

hydrogen, —C$_1$–C$_6$ alkyl, —OR$_2$, trifluoromethyl, phenyl, substituted C$_1$–C$_6$ alkyl where the substituents are selected from imidazolyl, phenyl, indolyl, p-hydroxyphenyl, —OR$_2$, 1 to 3 fluoro, —S(O)$_m$R$_2$, —C(O)OR$_2$, —C$_3$—C$_7$ cycloalkyl, —N(R$_2$)(R$_2$), —C(O)N(R$_2$)(R$_2$); or R$_7$ and R$_{7a}$ can independently be joined to one or both of R$_4$ and R$_5$ groups to form alkylene bridges between the terminal nitrogen and the alkyl portion of the R$_7$ or R$_{7a}$ groups, wherein the bridge contains 1 to 5 carbons atoms;

B, D, E, and F are independently selected from the group consisting of: —C(R$_8$)(R$_{10}$)—, —O—, C=O, —S(O)$_m$—, or —NR$_9$—, such that one or two of B, D, E, or F may be optionally absent to provide a 5, 6, or 7 membered ring; and provided that B, D, E and F can be —C(R$_8$)(R$_{10}$)— or C=O only when one of the remaining B, D, E and F groups is simultaneously —O—, —S(O)$_m$—, or —NR$_9$—, or B and D, or D and E taken together may be —N=CR$_{10}$— or —CR$_{10}$=N—, or B and D, or D and E taken together may be —CR$_8$=CR$_{10}$—, provided one of the other of B and E or F is simultaneously —O—, —S(O)$_m$—, or —NR$_9$—;

R$_8$ and R$_{10}$ are independently selected from the group consisting of:

hydrogen, —R$_2$, —OR$_2$, (—CH$_2$)$_q$-aryl, —(CH$_2$)$_q$—C(O)OR$_2$, —(CH$_2$)$_q$—C(O)O(CH$_2$)$_q$-aryl, or —(CH$_2$)$_q$—(1H-tetrazol-5-yl), where the aryl may be optionally substituted by 1 to 3 halo, 1 to 2 C$_1$–C$_8$ alkyl, 1 to 3 —OR$_2$ or 1 to 2 —C(O)OR$_2$;

R$_9$ is selected from the group consisting of:

—R$_2$, —(CH$_2$)$_q$-aryl, —C(O)R$_2$, —C(O)(CH$_2$)$_q$-aryl, —SO$_2$R$_2$,

—SO$_2$(CH$_2$)$_q$-aryl, —C(O)N(R$_2$)(R$_2$), —C(O)N(R$_2$)(CH$_2$)$_q$-aryl, —C(O)OR$_2$, 1-H-tetrazol-5-yl, —SO$_3$H, —SO$_2$NHC≡N, —SO$_2$N(R$_2$)aryl, —SO$_2$N(R$_2$)(R$_2$), and wherein the (CH$_2$)$_q$ may be optionally substituted by 1 to 2 C$_1$–C$_4$ alkyl, and the R$_2$ and aryl may be optionally further substituted by 1 to 3 —OR$_{2a}$, —O(CH$_2$)$_q$ aryl, 1 to 2 —C(O)OR$_{2a}$, 1 to 2 —C(O)O(CH$_2$)$_q$ aryl, 1 to 2 —C(O)N(R$_{2a}$)(R$_{2a}$), 1 to 2 —C(O)N(R$_{2a}$)(CH$_2$)$_q$ aryl, 1 to 5 halogen, 1 to 3 C$_1$–C$_4$ alkyl, 1,2,4-triazolyl, 1-H-tetrazol-5-yl, —C(O)NHSO$_2$R$_{2a}$, —S(O)$_m$R$_{2a}$, —C(O)NHSO$_2$(CH$_2$)$_q$-aryl, —SO$_2$NHC≡N, —SO$_2$NHC(O)R$_{2a}$, —SO$_2$NHC(O)(CH$_2$)$_q$aryl, —N(R$_2$)C(O)N(R$_{2a}$)(R$_{2a}$)(R$_{2a}$), —N(R$_2$a)C(O)N(R$_{2a}$)(CH$_2$)$_q$-aryl, —N(R$_{2a}$)(R$_{2a}$), —N(R$_{2a}$)C(O)R$_{2a}$, —N(R$_{2a}$)C(O)(CH$_2$)$_q$ aryl, —OC(O)N(R$_{2a}$)(R$_{2a}$), —OC(O)N(R$_{2a}$)(CH$_2$)$_q$ aryl, —SO$_2$(CH$_2$)$_q$ CONH—(CH$_2$)wNHC(O)R$_{11}$, wherein w is 2–6 and R$_{11}$ may be biotin, aryl, or aryl substituted by 1 or 2 OR$_2$, 1–2 halogen, azido or nitro;

m is 0, 1 or 2;

n is 1, or 2;

q may optionally be 0, 1, 2, 3, or 4; and

G, H, I and J are carbon, nitrogen, sulfur or oxygen atoms, such that at least one is a heteroatom and one of G, H, I or J may be optionally missing to afford a 5 or 6 membered heterocyclic aromatic ring; and pharmaceutically acceptable salts and individual diastereomers thereof.

Within this third class, the most preferred growth hormone secretagogues employed in the instant invention are realized in structural Formula V:

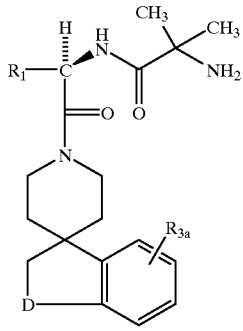

V

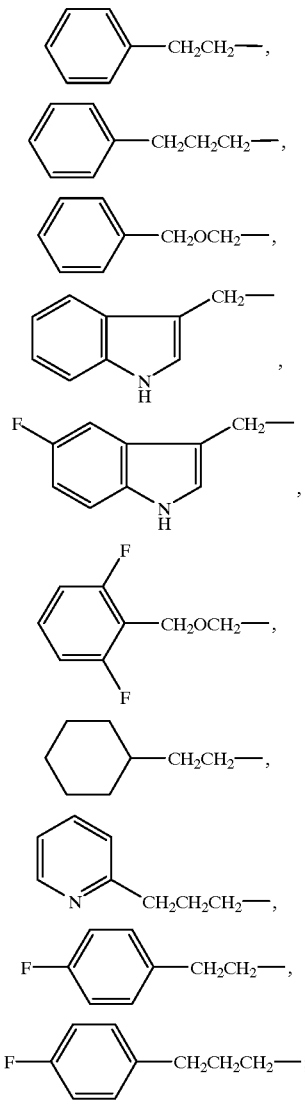

wherein R₁ is selected from the group consisting of:

$R_{3a}$ is H, or fluoro;

D is is selected from the group consisting of:
—O—, —S—, —S(O)$_m$—, N(R$_2$), NSO$_2$(R$_2$), NSO$_2$(CH$_2$)$_t$aryl, NC(O)(R$_2$),
NSO$_2$(CH$_2$)$_q$OH, NSO$_2$(CH$_2$)$_q$COOR$_2$, NSO$_2$(CH$_2$)$_q$C(O)—N(R$_2$)(R$_2$),

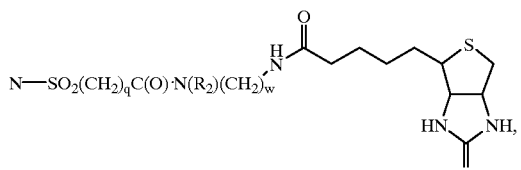

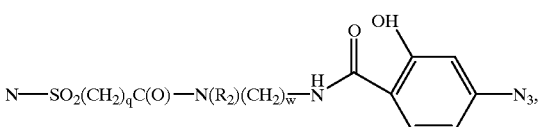

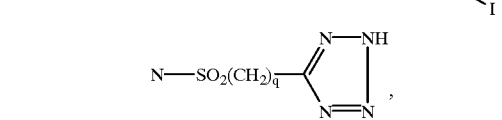

and the aryl is phenyl or pyridyl and the phenyl may be substituted by 1–2 halogen;
R$_2$ is H, or C$_1$–C$_4$ alkyl;
m is 1, 2;
t is 0, 1, or 2;
q is 1, 2, or 3;
w is 2, 3, 4, 5, or 6;
and the pharmaceutically acceptable salts and individual diastereomers thereof.

Representative most preferred growth hormone secretagoues within this third class which may be employed in the present invention include the following:

1) N-[1(R)-[(1,2-Dihydro-1-methanesulfonylspiro[3H-indole-3,4'-piperidin]-1'-yl)carbonyl]-2-(1H-indol-3-yl)ethyl]-2-amino-2-methylpropanamide;
2) N-[1(R)-[(1,2-Dihydro-1-methanecarbonylspiro[3H-indole-3,4'-piperidin]-1'-yl)carbonyl]-2-(1H-indol-3-yl)ethyl]-2-amino-2-methylpropanamide;
3) N-[1(R)-[(1,2-Dihydro-1-benzenesulfonylspiro[3H-indole-3,4'-piperidin]-1'-yl)carbonyl]-2-(1H-indol-3-yl)ethyl]-2-amino-2-methylpropanamide;
4) N-[1(R)-[(3,4-Dihydro-spiro[2H-1-benzopyran-2,4'-piperidin]-1'-yl)carbonyl]-2-(1H-indol-3-yl)ethyl]-2-amino-2-methylpropanamide;
5) N-[1(R)-[(2-Acetyl-1,2,3,4-tetrahydrospiro[isoquinolin-4,4'-piperidin]-1'-yl)carbonyl]-2-(indol-3-yl)ethyl]-2-amino-2-methyl-propanamide;
6) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide;
7) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide mesylate salt;
8) N-[1(R)-[(1,2-Dihydro-1-methanesulfonylspiro[3H-indole-3,4'-piperidin]-1'-yl)carbonyl]-2-(2',6'-difluorophenylmethyloxy)ethyl]-2-amino-2-methylpropanamide;
9) N-[1(R)-[(1,2-Dihydro-1-methanesulfonyl-5-fluorospiro[3H-indole-3,4'-piperidin]-1'-yl)carbonyl]-2-(phenylmethyloxy)ethyl]-2-amino-2-methylpropanamide;
10) N-[1(S)-[(1,2-Dihydro-1-methanesulfonylspiro[3H-indole-3,4'-piperidin]-1'-yl) carbonyl]-2-(phenylmethylthio)ethyl]-2-amino-2-methylpropanamide;

11) N-[1(R)-[(1,2-Dihydro-1-methanesulfonylspiro[3H-indole-3,4'-piperidin]-1'-yl)carbonyl]-3-phenylpropyl]-2-amino-2-methylpropanamide;
12) N-[1(R)-[(1,2-Dihydro-1-methanesulfonylspiro[3H-indole-3,4'-piperidin]-1'-yl)carbonyl]-3-cyclohexylpropyl]-2-amino-2-methylpropanamide;
13) N-[1(R)-[(1,2-Dihydro-1-methanesulfonylspiro[3H-indole-3,4'-piperidin]-1'-yl)carbonyl]-4-phenylbutyl]-2-amino-2-methylpropanamide;
14) N-[1(R)-[(1,2-Dihydro-1-methanesulfonylspiro[3H-indole-3,4'-piperidin]-1'-yl)carbonyl]-2-(5-fluoro-1H-indol-3-yl)ethyl]-2-amino-2-methylpropanamide;
15) N-[1(R)-[(1,2-Dihydro-1-methanesulfonyl-5-fluorospiro[3H-indole-3,4'-piperidin]-1'-yl)carbony]-2-(5-fluoro-1H-indol-3-yl)ethyl]-2-amino-2-methylpropanamide;
16) N-[1(R)-[(1,2-Dihydro-1-(2-ethoxycarbonyl)methylsulfonylspiro-[3H-indole-3,4'-piperidin]-1'-yl)carbonyl]-1-(1H-indol-3-yl)ethyl]-2-amino-2-methylpropanamide;
17) N-[1(R)-[(1,2-Dihydro-1,1-dioxospiro[3H-benzothiophene-3,4'-piperidin]-1'-yl)carbonyl]-2-(phenylmethyloxy)ethyl]-2-amino-2-methylpropanamide;

and pharmaceutically acceptable salts thereof.

Especially preferred growth hormone secretagogues within this third class which may be employed in the present invention include:

N-[1(R)-[(1,2-dihydro-1-methanesulfonylspiro[3H-indole-3,4'-piperidin]-1'-yl)carbonyl]-2-(phenylmethyloxy)ethyl]-2-amino-2-methylpropanamide;
N-[1(R)-[(1,2-dihydro-1-methanesulfonylspiro[3H-indole-3,4'-piperidin]-1'-yl)carbonyl]-2-(phenylmethyloxy)ethyl]-2-amino-2-methylpropanamide methanesulfonate; (ibutamoren mesylate)
N-[1(R)-[(1,2-dihydro-1-methanesulfonylspiro[3H-indole-3,4'-piperidin]-1'-yl)carbonyl]-3-phenylpropyl]-2-amino-2-methyl-propanamide;

and pharmaceutically acceptable salts thereof.

The most preferred compounds within this third class which may be employed in the present invention are identified as having the following structure:

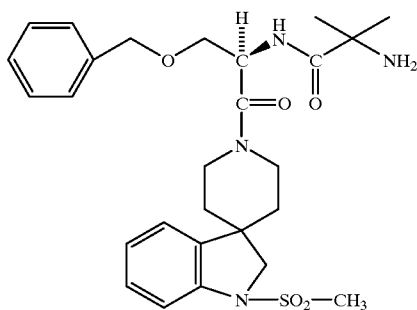

and pharmaceutically acceptable salts thereof, in particular, the methanesulfonate salt.

A representative fourth class of growth hormone secretagogues is disclosed in U.S. Pat. No. 5,492,916 as being compounds of the structural formula I:

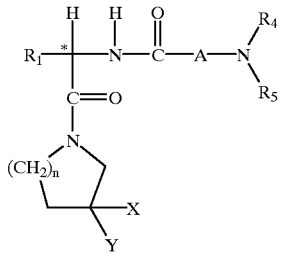

Formula I wherein the various substituents are as defined in U.S. Pat. No. 5,492,916.

Full descriptions of the preparation of the growth hormone secretagogues which may be employed in the present invention may be found in art, particularly the references cited herein.

In the above structural formulas and throughout the instant specification, the following terms have the indicated meanings:

The alkyl groups specified above are intended to include those alkyl groups of the designated length in either a straight or branched configuration which may optionally contain double or triple bonds. Exemplary of such alkyl groups are methyl, ethyl, propyl, ethinyl, isopropyl, butyl, sec-butyl, tertiary butyl, pentyl, isopentyl, hexyl, isohexyl, allyl, propenyl, butenyl, butadienyl and the like. The alkoxy groups specified above are intended to include those alkoxy groups of the designated length in either a straight or branched configuration which may optionally contain double or triple bonds. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propinyloxy, isobutenyloxy, 2-hexenyloxy, and the like. The term "halogen" is intended to include the halogen atom fluorine, chlorine, bromine and iodine. The term "aryl" is intended to include phenyl and naphthyl and aromatic residues of 5- and 6- membered rings with 1 to 3 heteroatoms or fused 5 or 6 membered bicyclic rings with 1 to 3 heteroatoms of nitrogen, sulfur or oxygen. Examples of such heterocyclic aromatic rings are pyridine, thiophene, benzothiophene, tetrazole, indole, N-methylindole, dihydroindole, indazole, N-formylindole, benzimidazole, thiazole, furan, pyrimidine, and thiadiazole.

Certain of the above defined terms may occur more than once in the above formula and upon such occurrence each term shall be defined independently of the other. Similarly, the use of a particular variable within a noted structural formula is intended to be independent of the use of such variable within a different structural formula.

For use in medicine, the salts of the compounds of this invention refer to non-toxic "pharmaceutically acceptable salts." Other salts may, however, be useful in the preparation of the compounds according to the invention or of their pharmaceutically acceptable salts. Salts encompassed within the term "pharmaceutically acceptable salts" refer to non-toxic salts of the compounds of this invention which are generally prepared by reacting the free base with a suitable organic or inorganic acid. Representative salts include the following: Acetate, Benzenesulfonate, Benzoate, Bicarbonate, Bisulfate, Bitartrate, Borate, Bromide, Calcium, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isothionate, Lactate, Lactobionate, Laurate, Malate, Maleate, Mandelate, Mesylate, Methylbromide, Methylnitrate, Methylsulfate, Mucate, Napsylate, Nitrate, N-methylglucamine ammonium salt, Oleate, Oxalate, Pamoate (Embonate), Palmitate, Pantothenate, Phosphate/diphosphate, Polygalacturonate, Salicylate, Stearate, Subacetate, Succinate, Sulfate, Sulfonate, Tannate, Tartrate, Teoclate, Tosylate, Triethiodide and Valerate. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

The compounds employed in the present invention, may have chiral centers and occur as racemates, racemic mixtures and as individual diastereomers, or enantiomers with all isomeric forms being included in the present invention. Therefore, where a compound is chiral, the separate enantiomers, substantially free of the other, are included within the scope of the invention; further included are all mixtures of the two enantiomers.

Full descriptions of the preparation of the growth hormone secretagoue employed in the present invention may be found e.g., in: U.S. Pat. No. 3,239,345; U.S. Pat. No. 4,036,979; U.S. Pat. No. 4,411,890; U.S. Pat. No. 5,206,235; U.S. Pat. No. 5,283,241; U.S. Pat. No. 5,284,841; U.S. Pat. No. 5,310,737; U.S. Pat. No. 5,317,017; U.S. Pat. No. 5,374,721; U.S. Pat. No. 5,430,144; U.S. Pat. No. 5,434,261; U.S. Pat. No. 5,438,136; U.S. Pat. No. 5,494,919; U.S. Pat. No. 5,494,920; U.S. Pat. No. 5,492,916; U.S. Pat. No. 5,536,716; EPO Patent Pub. No. 0,144,230; EPO Patent Pub. No. 0,513,974; PCT Patent Pub. No. WO 89/07110; PCT Patent Pub. No. WO 89/07111; PCT Patent Pub. No. WO 93/04081; PCT Patent Pub. No. WO 94/07486; PCT Patent Pub. No. WO 94/08583; PCT Patent Pub. No. WO 94/11012; PCT Patent Pub. No. WO 94/13696; PCT Patent Pub. No. WO 94/19367; PCT Patent Pub. No. WO 95/03289; PCT Patent Pub. No. WO 95/03290; PCT Patent Pub. No. WO 95/09633; PCT Patent Pub. No. WO 95/11029; PCT Patent Pub. No. WO 95/12598; PCT Patent Pub. No. WO 95/13069; PCT Patent Pub. No. WO 95/14666; PCT Patent Pub. No. WO 95/16675; PCT Patent Pub. No. WO 95/16692; PCT Patent Pub. No. WO 95/17422; PCT Patent Pub. No. WO 95/17423; PCT Patent Pub. No. WO 95/34311; PCT Patent Pub. No. WO 96/02530; PCT Patent Pub. No. WO 96/05195; PCT Patent Pub. No. WO 96/15148; PCT Patent Pub. No. WO 96/22782; PCT Patent Pub. No. WO 96/22997; PCT Patent Pub. No. WO 96/24580; PCT Patent Pub. No. WO 96/24587; PCT Patent Pub. No. WO 96/35713; PCT Patent Pub. No. WO 96/38471; PCT Patent Pub. No. WO 97/00894; PCT Patent Pub. No. WO 97/06803; PCT Patent Pub. No. WO 97/07117; *J. Endocrinol Invest.*, 15(Suppl 4), 45 (1992)); *Science,* 260 1640–1643 (Jun. 11, 1993); *Ann. Rep. Med. Chem.,* 28, 177–186 (1993); *Bioorg. Med. Chem. Ltrs.,* 4(22), 2709–2714 (1994); and *Proc. Natl. Acad. Sci. USA* 92, 7001–7005 (July 1995), as well as herein.

Methods to obtain the growth hormone releasing peptides GHRP-6 and GHRP-1 are described in U.S. Pat. No. 4,411,890 and PCT Patent Publications WO 89/07110, WO 89/07111, methods to obtain the growth hormone releasing peptide GHRP-2 are described in PCT Patent Publication WO 93/04081, and methods to obtain hexarelin are described in *J. Endocrinol Invest.,* 15(Suppl 4), 45 (1992).

The identification of a compound as a "growth hormone secretagogue" and thus able to directly or indirectly stimulate or increase the endogenous release of growth hormone in an animal may be readily determined without undue experimentation by methodology well known in the art, such as the assay described by Smith, et al., *Science,* 260, 1640–1643 (1993) (see text of FIG. 2 therein). In a typical experiment pituitary glands are aseptically removed from 150–200 g Wistar male rats and cultures of pituitary cells are prepared according to Cheng et al. *Endocrinol.,* 124, 2791–2798 (1989). The cells are treated with the subject compound and assayed for growth hormone secreting activity and intracellular cAMP levels as described by Chang et al. In particular, the intrinsic growth hormone secretagogue activity of a compounds which may be used in the present invention may be determined by this assay.

The term "therapeutically effective amount" shall mean that amount of a drug or pharmaceutical agent that will elicit the biological or medical response of a tissue, system, animal or human that is being sought by a researcher or clinician.

The term "acute deconditioning" is meant to indicate the presence of a diminished physical state in a patient characterized by muscle atrophy and muscle loss which results from specific insult such as immobilization or inactivity brought on by acute illness or injury. In contrast, chronic deconditioning refers to long-term muscle loss or wasting, i.e. sarcopenia.

The term "independent living" is meant to indicate that the patient is able to handle the physical demands of daily living with a minimal level of physical assistance from other persons. Patients living independently include, for example, patients who live in a private home or apartment and who do not receive formal or nonformal home health care services.

Accordingly, the present invention includes within its scope the use of a growth hormone secretagogue for enhancing the return of patients to independent living status following deconditioning, alone or in combination with other agents such as growth promoting and anabolic agents including TRH, diethylstilbesterol, amino acids, estrogens, β-agonists, theophylline, anabolic steroids, enkephalins, E series prostaglandins, retinoic acid, compounds disclosed in U.S. Pat. No. 3,239,345, e.g., zeranol, and compounds disclosed in U.S. Pat. No. 4,036,979, e.g., sulbenox. or peptides disclosed in U.S. Pat. No. 4,411,890, growth hormone releasing peptides GHRP-6, GHRP-1 and B-HT920 as well as hexarelin and GHRP-2 or growth hormone releasing hormone (GHRH, also designated GRF) and its analogs or growth hormone and its analogs or somatomedins including IGF-1 and IGF-2, (β-adrenergic agonists such as clonidine, serotonin 5HTID agonists such as sumitriptan or agents which inhibit somatostatin or its release such as physostigmine and pyridostigmine. In particular, the growth hormone secretagogue may be used in combination with growth hormone releasing factor, an analog of growth hormone releasing factor, IGF-1, or IGF-2.

This particular application of growth hormone secretagogues provides unexpected benefit relative to the administration of exogenous growth hormone. In particular, the growth hormone secretagogue enhances the normal pulsatile releases of endogenous growth hormone and thus is more likely to reproduce the natural pattern of endogenous growth hormone release, especially with regard to increasing the level of endogenous growth hormone prior to or in during the initial onset of sleep. Growth hormone secregagogues which are orally active also have the benefit being able to be administered orally, rather than just intravenously, intraperitoneally or subcutaneously.

In addition, the present invention includes within its scope a pharmaceutical composition for enhancing the return of patients to independent living status following acute deconditioning comprising, as an active ingredient, at least one growth hormone secretagogues in association with a pharmaceutical carrier or diluent. Optionally, the active ingredient of the pharmaceutical compositions can comprise an anabolic agent in addition to at least one growth hormone secretagogue or another composition which exhibits a different activity, e.g., an antibiotic growth promoting agent or in combination with a corticosteroid to minimize the catabolic side effects or with other pharmaceutically active materials wherein the combination enhances efficacy and minimizes side effects. Growth promoting and anabolic agents include, but are not limited to, TRH, diethylstilbesterol, estrogens, β-agonists, theophylline, anabolic steroids, dehydroepiandrosterone, enkephalins, E series prostaglandins, retinoic acid, compounds disclosed in U.S. Pat. No. 3,239,345, e.g., zeranol, and compounds disclosed in U.S. Pat. No. 4,036,979, e.g., sulbenox. or peptides disclosed in U.S. Pat. No. 4,411,890.

The present invention further includes the use of a growth hormone secretagogue, alone or in combination with another agent, in the manufacture of a medicament for enhancing the return of patients to independent living status following acute deconditioning.

In addition, the present invention contemplates the use of a growth hormone secretagogue for enhancing the return of patients to independent living status following deconditioning in combination with another growth hormone secretagogues such as those referenced herein, including the growth hormone releasing peptides GHRP-6 and GHRP-1 (described in U.S. Pat. No. 4,411,890 and PCT publications WO 89/07110, WO 89/07111) and GHRP-2 (described in WO 93/04081) and B-HT920, as well as hexarelin or growth hormone releasing hormone (GHRH, also designated GRF) and its analogs, or growth hormone and its analogs, or somatomedins including IGF-1 and IGF-2, or with (α-adrenergic agonists such as clonidine or serotonin 5HTD agonists such as sumatriptan, or agents which inhibit somatostatin or its release such as physostigmine and pyridostigmine. For example, a growth hormone secretagogue may be used in combination with IGF-1 for enhancing the return of patients to independent living status following deconditioning.

It will be known to those skilled in the art that other compounds may be used in an effort to enhance the return of patients to independent living status following deconditioning. Combinations of these therapeutic agents some of which have also been mentioned herein with a growth hormone secretagogue will bring additional, complementary, and often synergistic properties to enhance the desirable properties of these various therapeutic agents. In these combinations, the growth hormone secretagogue and the therapeutic agents may be independently present in dose ranges from one one-hundredth to one times the dose levels which are effective when these compounds and secretagogues are used singly.

Typically, the individual daily dosages for these combinations may range from about one-fifth of the minimally recommended clinical dosages to the maximum recommended levels for the entities when they are given singly.

To illustrate these combinations, a growth hormone secretagogue effective clinically effective clinically at a given daily dose range may be effectively combined, at levels which are equal or less than the daily dose range, with the following compounds at the indicated per day dose range: and salts thereof, and combinations thereof, and the like.

Naturally, these dose ranges may be adjusted on a unit basis as necessary to permit divided daily dosage and, as noted above, the dose will vary depending on the nature and severity of the disease, weight of patient, special diets and other factors.

Anabolic effects especially in the treatment of geriatric male patients are obtained with compounds of this invention in combination with anabolic steroids such as dehydroepiandrosterone, oxymetholone, methyltesterone, fluoxymesterone, restosterone and stanozolol.

These combinations may be formulated into pharmaceutical compositions as known in the art and as discussed below.

A growth hormone secretagogue may be administered alone or in combination by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. In the case of capsules, tablets and pills, the dosage forms may also comprise buffering agents. When the dosage unitform is a capsule, it may contain, in addition to materials of the above type, a liquid carrier such as fatty oil. Various other materials may be present as coatings or to otherwise modify the physical form of the dosage unit. Tablets and pills can additionally be prepared with enteric coatings and tablets may be coated with shellac, sugar or both.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring, and perfuming agents. A syrup or elixir may contain the active compound, sucrose as a sweetening agent, methyl and propyl parabens as preservatives, a dye and a flavoring such as cherry or orange flavor.

Preparations according to this invention for parenteral administration include sterile aqueous or non-aqueous solutions, suspensions, or emulsions. Sterile compositions for injection may be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like may be incorporated as required. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use. Compositions for rectal or vaginal administration are preferably suppositories which may contain, in addition to the active substance, excipients such as cocoa butter or a suppository wax. Compositions for nasal or sublingual administration are also prepared with standard excipients well known in the art.

The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.0001 to 10 mg/kg. of body weight daily are administered to patients and animals, e.g., mammals, to obtain effective release of growth hormone. The dosage range will generally be about 0.5 mg to 1.0 g. per patient per day which may be administered in single or multiple doses. Perferably, the dosage range will be about 0.5 mg to 500 mg per patient per day; more preferably about 0.5 mg to 200 mg per patient per day; and even more preferably about 5 mg to 50 mg per patient per day. Pharmaceutical compositions of the present invention may be provided in a solid dosage formulation preferably comprising about 0.5 mg to 500 mg active ingredient, more preferably comprising about 1 mg to 250 mg active ingredient. The pharmaceutical composition is preferably provided in a solid dosage formulation comprising about 1 mg, 5 mg, 10 mg, 25 mg, 50 mg, 100 mg, 200 mg or 250 mg active ingredient.

The following examples are provided for the purpose of further illustration only and are not intended to be limitations on the disclosed invention.

EXAMPLE 1

Double-Blind, Placebo-Controlled, Parallel-Group Study to Determine the Effect of a Growth Hormone Secretagogue on the Return to Independent Living Status in Patients Suffering a Hip Fracture In this study, hip fracture is a model state of acute deconditioning in the elderly for determining the effect of a growth hormone secretagogue in return of patients to independent living status.

Approximately 168 postoperative hip fracture patients were enrolled in this study. Patients were between 3 and 14 days postoperative hip repair. Patients included both males and females over 65 years of age who have ambulatory prefracture (with or without assistance), with need for assistance and level of premorbid ambulation documented. Their fracture was of nonpathological origin, e.g., it resulted from a fall or accident rather than from neoplasm.

The subjects received either a placebo or 25 mg of the growth hormone secretagogue N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methyl-propanamide mesylate P.O., daily in the morning, for a total duration of 6 months. The study was initiated between 3 and 14 days following surgery to repair their hip fracture. All subjects received standard-of-care post-operative physical rehabilitation. Follow-up of subjects was conducted 6 months after cessation of treatment (i.e. in Months 7–12).

Patients completed a personal profile questionnaire at 2, 6, 13, 20, and 26 weeks following initiation of treatment and at 52 weeks following initiation of treatment (i.e. 6 months after cessation of treatment). The questionnaires compared the subject's pre-fracture status and post-fracture status with respect to housing and degree of care which they received. The questionnaire for pre-fracture status determined where the particular subject was living before their hip fracture (i.e. in a private home/apartment, an assisted living center, a nursing home, or other living situation) and whether they received home health care services. The questionnaire for post-fracture status determined where the particular subject was living and had lived after their hip fracture (i.e. in a private home/apartment, an assisted living center, a nursing home, a rehabilitation hospital/center, an acute care hospital, a chronic medical care center, or other living situation) and whether they received home health care services.

Specific demographics for the group receiving the growth hormone secretagogue: Initial randomization=84 patients; Completed Month 6=62 patients; Completed Month 12=61 patients; Age=79.1±7.3 yrs.; Gender=79 Females, 21 Males; Independent Pre-Fracture=64%.

Specific demographics for the group receiving placebo: Initial randomization=77 patients; Completed Month 6=69 patients; Completed Month 12=65 patients; Age=79.1±7.2 yrs.; Gender=78 Females, 22 Males; Independent Pre-Fracture=72%.

The data from this study is summarized in FIGS. 1 and 2.

FIG. 1 depicts a summary of the data regarding living independence from a double-blind, placebo-controlled, parallel-group study to determine the effect of a growth hormone secretagogue on the return to independent living status in patients suffering a hip fracture. The percentage of patients living independently is presented with respect to the number of weeks since the patient initiated the study.

Following their hip fracture, a greater percentage of the patients receiving growth hormone secretagogue ("Compound") were living independently (i.e. living at home with no assistance) following their hip fracture.

FIG. 2 depicts a summary of the data regarding the return to independent living status from a double-blind, placebo-controlled, parallel-group study to determine the effect of a growth hormone secretagogue on the return to independent living status in patients suffering a hip fracture. The percentage of patients living independently is presented with respect to the number of weeks since the patient initiated the study.

Of the patients who were living independently prior to their hip fracture, a greater percentage of these patients receiving growth hormone secretagogue ("Compound") returned to independence (i.e. living at home with no assistance) following their hip fracture.

Overall, of the patients who were living independently at baseline, approximately 64% of the placebo group versus 83% of the group receiving the growth hormone secretagogue (p=0.036) returned to independent function at the end of the study.

The results of the foregoing study indicate that the administration of the growth hormone secretagogue had a positive effect with respect to enhancing the return of patients to independent living status following acute deconditioning, specifically hip fracture. The results observed in this study would clearly extend to other growth hormone secretagogues and for other conditions associated with acute deconditioning.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed:

1. A method for enhancing the return of a patient to independent living status following acute deconditioning of the patient who was living independently prior to such acute deconditioning which comprises administering to the patient an effective amount of a growth hormone secretagogue.

2. The method of claim 1 wherein the growth hormone secretagogue is an orally active growth hormone secretagogue.

3. The method of claim 2 wherein the growth hormone secretagogue is orally administered.

4. The method of claim 1 wherein the growth hormone secretagogue is a non-peptidal growth hormone secretagogue.

5. The method of claim 1 wherein the patient is a human.

6. The method of claim 4 wherein the acute deconditioning is the result of surgery, immobilization or a major injury.

7. The method of claim 4 wherein the acute deconditioning is the result of a hip fracture.

8. The method of claim 1 wherein the growth hormone secretagogue is selected from the group consisting of:

Formula I

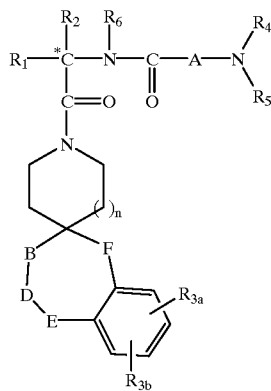

-continued

Formula II

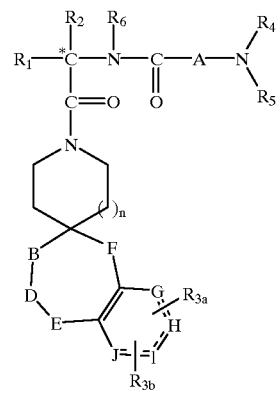

wherein:

$R_1$ is selected from the group consisting of:
—$C_1$–$C_{10}$ alkyl, -aryl, -aryl-($C_1$–$C_6$ alkyl),
—$C_3$–$C_7$ cycloalkyl-($C_1$–$C_6$ alkyl), —$C_1$–$C_5$ alkyl-K—$C_1$–$C_5$ alkyl, -aryl($C_0$–$C_5$ alkyl)-K—($C_1$–$C_5$ alkyl),
—$C_3$–$C_7$ cycloalkyl($C_0$–$C_5$ alkyl)-K—($C_1$–$C_5$ alkyl),
wherein K is O, $S(O)_m$, $N(R_2)C(O)$, $C(O)N(R_2)$, $OC(O)$, $C(O)O$, or —$CR_2$=$CR_2$—, or —C≡C—,
and wherein the aryl groups are as defined below and the $R_2$ and alkyl groups may be further substituted by 1 to 9 halogen, $S(O)mR_{2a}$, 1 to 3 $OR_{2a}$, or $C(O)OR_{2a}$, and the aryl groups may be further substituted by phenyl, phenoxy, halophenyl, 1–3 $C_1$–$C_6$ alkyl, 1 to 3 halogen, 1 to 2 —$OR_2$, methylenedioxy, —$S(O)_mR_2$, 1 to 2 —$CF_3$, —$OCF_3$, nitro, —$N(R_2)(R_2)$, —$N(R_2)C(O)R_2$, —$C(O)OR_2$, —$C(O)N(R_2)(R_2)$, —$SO_2N(R_2)(R_2)$, —$N(R_2)S(O)_2$ aryl, and —$N(R_2)SO_2R_2$;

$R_2$ is selected from the group consisting of:
hydrogen, $C_1$–$C_6$ alkyl, $C_3$–$C_7$ cycloalkyl, and where two $C_1$–$C_6$ alkyl groups are present on one atom, they may be optionally joined to form a $C_3$–$C_8$ cyclic ring optionally including oxygen, sulfur or $NR_{2a}$;

$R_{2a}$ is hydrogen, or $C_1$–$C_6$ alkyl;

$R_{3a}$ and $R_{3b}$ are independently selected from the group consisting of:
hydrogen, halogen, —$C_1$–$C_6$ alkyl, —$OR_2$, cyano, —$OCF_3$, methylenedioxy, nitro, —$S(O)_mR$, —$CF_3$ or —$C(O)OR_2$ and when $R_{3a}$ and $R_{3b}$ are in an ortho arrangement, they may be joined to form a $C_5$ to $C_8$ aliphatic or aromatic ring optionally including 1 or 2 heteroatoms selected from oxygen, sulfur or nitrogen;

$R_4$ and $R_5$ are independently selected from the group consisting of:
hydrogen, —$C_1$–$C_6$ alkyl, substituted $C_1$–$C_6$ alkyl wherein the substituents are selected from 1 to 5 halo, 1 to 3 hydroxy, 1 to 3 $C_1$–$C_{10}$ alkanoyloxy, 1 to 3 $C_1$–$C_6$ alkoxy, phenyl, phenoxy, 2-furyl, $C_1$–$C_6$ alkoxycarbonyl, —$S(O)_m$($C_1$–$C_6$ alkyl); or $R_4$ and $R_5$ can be taken together to form —($CH_2$)$_r$$L_a$($CH_2$)$_s$— where $L_a$ is —$C(R_2)_2$—, —O—, —$S(O)_m$—, or —$N(R_2)$—,
where r and s are independently 1 to 3 and $R_2$ is as defined above;

$R_6$ is hydrogen or $C_1$–$C_6$ alkyl;

A is:

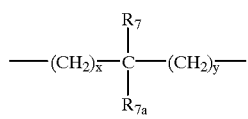

or

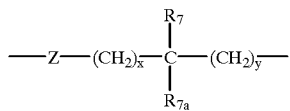

wherein x and y are independently 0–3;

Z is N—$R_2$ or O;

$R_7$ and $R_{7a}$ are independently selected from the group consisting of:

hydrogen, —$C_1$–$C_6$ alkyl, —$OR_2$, trifluoromethyl, phenyl, substituted $C_1$–$C_6$ alkyl where the substituents are selected from imidazolyl, phenyl, indolyl, p-hydroxyphenyl, —$OR_2$, 1 to 3 fluoro, —$S(O)_mR_2$, —$C(O)OR_2$, —$C_3$–$C_7$ cycloalkyl, —$N(R_2)(R_2)$, —$C(O)N(R_2)(R_2)$; or $R_7$ and $R_{7a}$ can independently be joined to one or both of $R_4$ and $R_5$ groups to form alkylene bridges between the terminal nitrogen and the alkyl portion of the $R_7$ or $R_{7a}$ groups, wherein the bridge contains 1 to 5 carbons atoms;

B, D, E, and F are independently selected from the group consisting of:

—$C(R_8)(R_{10})$—, —O—, C=O, —$S(O)_m$—, or —$NR_9$—, such that one or two of B, D, E, or F may be optionally absent to provide a 5, 6, or 7 membered ring; and provided that B, D, E and F can be —$C(R_8)(R_{10})$— or C=O only when one of the remaining B, D, E and F groups is simultaneously —O—, —$S(O)_m$—, or —$NR_9$—, or B and D, or D and E taken together may be —N=$CR_{10}$— or —$CR_{10}$=N—, or B and D, or D and E taken together may be —$CR_8$=$CR_{10}$—, provided one of the other of B and E or F is simultaneously —O—, —$S(O)_m$—, or —$NR_9$;

$R_8$ and $R_{10}$ are independently selected from the group consisting of:

hydrogen, —$R_2$, —$OR_2$, (—$CH_2$)$_q$-aryl, —$(CH_2)_q$—C(O)O$R_2$, —$(CH_2)_q$—C(O)O(CH$_2$)$_q$-aryl, or —$(CH_2)_q$-(1H-tetrazol-5-yl), where the aryl may be optionally substituted by 1 to 3 halo, 1 to 2 $C_1$–$C_8$ alkyl, 1 to 3 —$OR_2$ or 1 to 2 —$C(O)OR_2$;

$R_9$ is selected from the group consisting of:

—$R_2$, —$(CH_2)_q$-aryl, —$C(O)R_2$, —$C(O)(CH_2)_q$-aryl, —$SO_2R_2$, —$SO_2(CH_2)_q$-aryl, —$C(O)N(R_2)(R_2)$, —$C(O)N(R_2)(CH_2)_q$-aryl, —$C(O)OR_2$, 1-H-tetrazol-5-yl, —$SO_3H$, —$SO_2NHC\equiv N$, —$SO_2N(R_2)$aryl, —$SO_2N(R_2)(R_2)$, and wherein the (CH$_2$)$_q$ may be optionally substituted by 1 to 2 $C_1$–$C_4$ alkyl, and the $R_2$ and aryl may be optionally further substituted by 1 to 3 —$OR_{2a}$, —$O(CH_2)_q$ aryl, 1 to 2 —$C(O)OR_{2a}$, 1 to 2 —$C(O)O(CH_2)_q$ aryl, 1 to 2 —$C(O)N(R_{2a})(R_{2a})$, 1 to 2 —$C(O)N(R_{2a})(CH_2)_q$ aryl, 1 to 5 halogen, 1 to 3 $C_1$–$C_4$ alkyl, 1,2,4-triazolyl, 1-H-tetrazol-5-yl, —$C(O)$NHSO$_2R_{2a}$, —$S(O)_mR_{2a}$, —$C(O)$NHSO$_2(CH_2)_q$-aryl, —$SO_2NHC\equiv N$, —$SO_2NHC(O)R_{2a}$, -$SO_2NHC(O)$(CH$_2$)$_q$aryl, —$N(R_2)C(O)N(R_{2a})(R_{2a})$, —$N(R_{2a})C(O)N(R_{2a})(CH_2)_q$-aryl, —$N(R_{2a})(R_{2a})$, —$N(R_{2a})C(O)R_{2a}$, —$N(R_{2a})C(O)(CH_2)_q$ aryl, —$OC(O)N(R_{2a})(R_{2a})$, —$OC(O)N(R_{2a})(CH_2)_q$ aryl, —$SO_2(CH_2)_q$CONH—(CH$_2$)wNHC(O)$R_{11}$, wherein w is 2–6 and $R_{11}$ may be biotin, aryl, or aryl substituted by 1 or 2 $OR_2$, 1–2 halogen, azido or nitro;

m is 0, 1 or 2;

n is 1, or 2;

q may optionally be 0, 1, 2, 3, or 4; and

G, H, I and J are carbon, nitrogen, sulfur or oxygen atoms, such that at least one is a heteroatom and one of G, H, I or J may be optionally missing to afford a 5 or 6 membered heterocyclic aromatic ring; and pharmaceutically acceptable salts and individual diastereomers thereof.

9. The method of claim 1 wherein the growth hormone secretagogue is selected from the group consisting of:

1) N-[1(R)-[(1,2-Dihydro-1-methanesulfonylspiro[3H-indole-3,4'-piperidin]-1'-yl)carbonyl]-2-(1H-indol-3-yl)ethyl]-2-amino-2-methylpropanamide;

2) N-[1(R)-[(1,2-Dihydro-1-methanecarbonylspiro[3H-indole-3,4'-piperidin]-1'-yl )carbonyl]-2-(1H-indol-3-yl)ethyl]-2-amino-2-methylpropanamide;

3) N-[1(R)-[(1,2-Dihydro-1-benzenesulfonylspiro[3H-indole-3,4'-piperidin]-1'-yl)carbonyl]-2-(1H-indol-3-yl)ethyl]-2-amino-2-methylpropanamide;

4) N-[1(R)-[(3,4-Dihydro-spiro[2H-1-benzopyran-2,4'-piperidin]-1'-yl) carbonyl]-2-(1H-indol-3-yl)ethyl]-2-amino-2-methylpropanamide;

5) N-[1(R)-[(2-Acetyl-1,2,3,4-tetrahydrospiro[isoquinolin-4,4'-piperidin]-1'-yl)carbonyl]-2-(indol-3-yl)ethyl]-2-amino-2-methyl-propanamide;

6) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide;

7) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide mesylate salt;

8) N-[1(R)-[(1,2-Dihydro-1-methanesulfonylspiro[3H-indole-3,4'-piperidin]-1'-yl)carbonyl]-2-(2',6'-difluorophenylmethyloxy)ethyl]-2-amino-2-methylpropanamide;

9) N-[1(R)-[(1,2-Dihydro-1-methanesulfonyl-5-fluorospiro[3H-indole-3,4'-piperidin]-1'-yl)carbonyl]-2-(phenylmethyloxy)ethyl]-2-amino-2-methylpropanamide;

10) N-[1(S)-[(1,2-Dihydro-1-methanesulfonylspiro[3H-indole-3,4'-piperidin]-1'-yl) carbonyl]-2-(phenylmethylthio)ethyl]-2-amino-2-methylpropanamide;

11) N-[1(R)-[(1,2-Dihydro-1-methanesulfonylspiro[3H-indole-3,4'-piperidin]-1'-yl)carbonyl]-3-phenylpropyl]-2-amino-2-methylpropanamide;

12) N-[1(R)-[(1,2-Dihydro-1-methanesulfonylspiro[3H-indole-3,4'-piperidin]-1'-yl)carbonyl]-3-cyclohexylpropyl]-2-amino-2-methylpropanamide;

13) N-[1(R)-[(1,2-Dihydro-1-methanesulfonylspiro[3H-indole-3,4'-piperidin]-1'-yl)carbonyl]-4-phenylbutyl]-2-amino-2-methylpropanamide;

14) N-[1(R)-[(1,2-Dihydro-1-methanesulfonylspiro[3H-indole-3,4'-piperidin]-1'-yl)carbonyl]-2-(5-fluoro-1H-indol-3-yl)ethyl]-2-amino-2-methylpropanamide;

15) N-[1(R)-[(1,2-Dihydro-1-methanesulfonyl-5-fluorospiro[3H-indole-3,4'-piperidin]-1'-yl)carbonyl]-2-(5-fluoro-1H-indol-3-yl)ethyl]-2-amino-2-methylpropanamide;
16) N-[1(R)-[(1,2-Dihydro-1-(2-ethoxycarbonyl) methylsulfonylspiro-[3H-indole-3,4'-piperidin]-1'-yl)carbonyl]-2-(1H-indol-3-yl)ethyl]-2-amino-2-methylpropanamide;
17) N-[1(R)-[(1,2-Dihydro-1,1-dioxospiro[3H-benzothiophene-3,4'-piperidin]-1'-yl)carbonyl]-2-(phenylmethyloxy)ethyl]-2-amino-2-methylpropanamide; and pharmaceutically acceptable salts thereof.

10. The method of claim 1 wherein the growth hormone secretagogue is selected from the group consisting of:
N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide; and pharmaceutically acceptable salts thereof.

11. The method of claim 1 wherein the growth hormone secretagogue is:
N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide mesylate salt.

12. The method of claim 1 wherein the growth hormone secretagogue is selected from the group consisting of: H H C=O 0 and pharmaceutically acceptable salts thereof.

13. The method of claim 1 wherein the growth hormone secretagogue is:

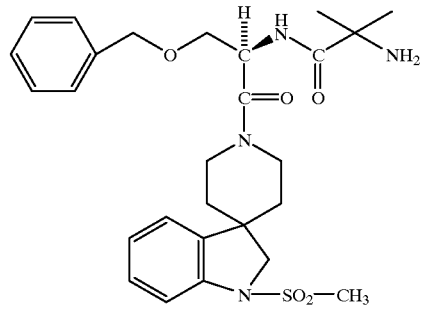

methanesulfonate salt.

14. The method of claim 1 where administration of the growth hormone secretagogue is in conjunction with physical therapy.

15. The method of claim 4 wherein the compound is administered in conjunction with recombinant growth hormone or an additional growth hormone secretagogue which is selected from the group consisting of: GHRP-6, GHRP-1, GHRP-2, growth hormone releasing factor; an analog of growth hormone releasing factor; IGF-1; and IGF-2.

* * * * *